United States Patent [19]

Hardtmann

[11] 3,937,705
[45] Feb. 10, 1976

[54] 1-ISOPROPYL-7-METHYL-4-(P-FLUORO-PHENYL)-2(1H)-QUINAZOLINONE
[75] Inventor: Goetz E. Hardtmann, Florham Park, N.J.
[73] Assignee: Sandoz, Inc., E. Hanover, N.J.
[22] Filed: July 3, 1974
[21] Appl. No.: 485,360

Related U.S. Application Data
[63] Continuation of Ser. No. 233,289, March 9, 1972, abandoned.

[52] U.S. Cl.... 260/251 QB; 260/251 A; 260/465 G; 260/562 B; 260/566 R; 260/570 AB; 424/251
[51] Int. Cl.² .................................... C07D 239/82
[58] Field of Search ............................ 260/251 QB

[56] References Cited
UNITED STATES PATENTS
3,549,635  12/1970  Ott ................................. 260/251
3,562,272  2/1971  Ott ................................. 260/251
3,723,432  3/1973  Ott ................................. 260/251 QB
3,759,920  9/1973  Linder et al. .................. 260/251 QB Primary Examiner—Raymond V. Rush
Attorney, Agent, or Firm—Gerald D. Sharkin; Richard E. Vila

[57] ABSTRACT

1-isopropyl-7-methyl-4-(p-fluorophenyl)-2(1H)-quinazolinone useful, for example, as a highly active anti-inflammatory agent of extended half line. The compound may be prepared by any of several processes, e.g. by reacting a 2-isopropylamino-4-methylbenzophenone with potassium isocyanate.

1 Claim, No Drawings

1-ISOPROPYL-7-METHYL-4-(P-FLUORO-PHENYL)-2(1H)-QUINAZOLINONE

This is a continuation of application Ser. No. 233,289 filed Mar. 9, 1972, now abandoned.

The present invention relates to the compound 1-isopropyl-7-methyl-4-(p-fluorophenyl)-2(1H)-quinazolinone having the structural formula I:

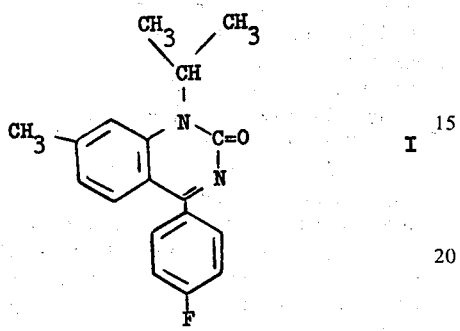

I

The invention also relates to the use of such compound as a pharmaceutical agent, e.g. as an anti-inflammatory agent having potent and long acting anti-inflammatory activity.

The compound of the invention may be prepared:

a. by cyclizing a compound of the formula II:

II with a compound selected from the group of:
i. a $C_{1-5}$ alkyl carbamate
ii. urea
iii. carbamyl chloride
iv. isocyanic acid,
at an elevated temperature, provided that when a $C_{1-5}$ alkyl carbamate is employed, the process is effected at a temperature of at least 140°C and in the presence of a catalytic amount of a Lewis acid, or b. by cyclizing a compound of the formula II, above, by reaction with an acid chloride or bromide and a compound of the formula III:

$$M-N=C=O \quad \text{III}$$

in which M signifies an alkali metal or alkaline earth metal, or the ammonium cation,
or with the reaction product of an acid chloride or bromide and a compound of the formula III, above stated, c. by cyclizing a compound of the formula IV

IV with a carbonic acid derivative selected from the group of:
i. a $C_{1-5}$ alkyl chlorocarbonate,
ii. a $C_{1-5}$ alkyl carbamate,
iii. a 1,1'-carbonyldiimidazole, and
iv. phosgene, or d. by oxidizing a compound of the formula V:

V in which Z is oxygen or sulfur, or e. by reacting a compound of the formula VI,

VI in which M' signifies an alkali metal atom, with a compound of the formula VII:

$$X'-CH\begin{smallmatrix}-CH_3\\-CH_3\end{smallmatrix} \quad \text{VII}$$

in which X' signifies a chlorine, bromine or iodine atom, in the presence of an organic solvent which is inert under the reaction conditions, or f. by reacting a compound of the formula VIII:

VIII in which Y' signifies a fluorine, chlorine or bromine atom, with ammonia, or g. by hydrolyzing a compound of the formula IX:

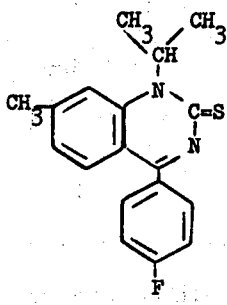

at a temperature of from 10°C. to 150°C., or h. by dehydrogenating a compound of the formula X:

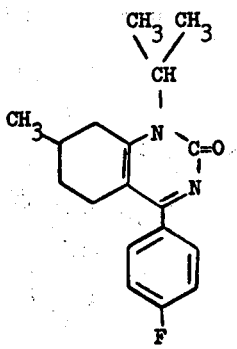

Process (a)(i) is conveniently carried out at a temperature of from 140°C. to 200°C., the preferred Lewis acid being zinc chloride and the preferred carbamate being ethyl carbamate. If desired, the reaction may be carried out in an organic solvent which is inert under the reaction conditions, e.g. o-dichlorobenzene, but this is not necessary since an excess of the carbamate can be used for this purpose. Depending on the particular conditions employed, a suitable reaction time is from about 30 minutes to about 4 hours.

Process (a)(ii) is conveniently carried out at temperatures in the range of from 80°C. to 220°C. In one manner of effecting the process, the reaction may be carried out in the absence of added solvent at a temperature of from 140°C. to 220°C., preferably 180°C. to 210°C., as described in Japanese Pat. No. 20865/63, published Sept. 16, 1963. In another and more preferred mode of effecting the process, the reaction is carried out at temperatures of from 80°C. to 160°C., preferably 100°C. to 130°C., conveniently at the reflux temperature of the system, in the presence of a lower monocarboxylic acid of 2 to 4 carbon atoms, preferably acetic acid, the mol ratio of urea to the compound II being at least 3:1 up to 20:1 or more, preferably 4:1 to 15:1, and more preferably 5:1 to 10:1, and the mol ratio of carboxylic acid to urea being at least 2:1, preferably 4:1 to 12:1.

Process (a)(iii) may be effected conveniently at temperatures in the range of 140°C. to 220°C. in similar manner to that in which process (a)(ii) may be carried out in absence of a solvent.

Process (a)(iv) is suitably effected at a temperature of from 50°C. to 150°C., preferably 100°C. to 140°C. The isocyanic acid is well known to be unstable and are therefore desirably prepared in situ. Thus, the process may be effected in acidic medium employing a salt of the isocyanic acid, preferably an alkali metal, e.g. sodium or potassium salt or most preferably, the ammonium salt. The acid employed to produce in situ the desired isocyanic acid from the salt is preferably a lower carboxolic acid, desirably acetic acid, which may also be conveniently employed as a solvent for the reaction.

Process (b) is conveniently effected in an organic solvent which is inert under the reaction conditions, at a temperature of from 10°C. to 80°C., preferably 30°C. to 70°C. As indicated, the process may be effected by reacting a compound of formula II with the reaction product of an acid chloride or bromide and a compound of formula III and it is generally preferred to first react the acid halide and compound of formula III and then add the compound of formula II to the resulting reaction mixture. The reaction of the acid halide and compound III is exothermic and is preferably initiated at a temperature of from 10°C. to 30°C. It will be understood that the acid halides employed should not carry substituents or functional groups which would interfere with the process. Suitable acid halides include acetyl chloride and benzoyl chloride, preferably benzoyl chloride. Naturally, the most suitable compounds of formula III are those most readily reacting with the acid halide to eliminate, as a by-product, a halide of the cation M. Suitably, the compound of formula III is an alkali metal isocyanate such as sodium isocyanate or ammonium isocyanate, and preferably ammonium isocyanate. Suitable solvents included lower alcohols, ketones and cyclic ethers, acetone being preferred. Treatment of the resulting reaction mixture with a strong base such as aqueous sodium hydroxide at elevated temperatures may be employed to enhance the cyclization which yields the desired product.

Process (c)(i) involving reaction of a compound of formula IV with methyl chlorocarbonate or ethyl chlorocarbonate, preferably ethyl chlorocarbonate, may be suitably carried out at a temperature of from 30°C. to 150°C., preferably 60°C. to 100°C. The reaction may be carried out in an organic solvent which is inert under the reaction conditions, suitably an aromatic hydrocarbon, e.g. benzene, toluene, or xylene, preferably benzene. Other suitable solvents include dioxane. The mole ratio of the chlorocarbonate to the compound of formula IV is not critical but the reaction is preferably carried out with a substantial excess of the chlorocarbonate. The reaction time may, for example, range from ½ hour to 10 hours, more usually 1 to 4 hours. The cyclisation with the chlorocarbonate may be optionally carried out in the presence of an acid-binding agent such as an inorganic base, e.g. sodium carbonate or potassium carbonate, or a tertiary amine, e.g. a trialkylamine or pyridine, more preferably triethylamine.

Process (c)(ii) is suitably carried out at a temperature of from 140° to 200°C., preferably 160° to 180°C. The mole ratio of the alkyl carbamate, preferably urethane, to the compound of formula IV is not critical. In the preferred forms of practice, there is employed a substantial excess of carbamate which also serves as the preferred solvent for the reaction. Other suitable high-boiling organic solvents which are inert under the reaction conditions may alternatively or additionally be employed, if desired. The reaction time may for example range for ½ to 10 hours, more usually 1 to 4 hours. The cyclisation with the carbamate is optionally and preferably conducted in the presence of a Lewis acid as catalyst for the reaction. The amount of Lewis acid employed is preferably between 5% to 20% based on the weight of compound in the reaction mixture. The preferred catalyst is zinc chloride.

Process (c) (iii) is suitably carried out at a temperature of from 20°C. to 120°C., preferably 60°C. to 90°C. The reaction is preferably carried out in an organic solvent which is inert under the reaction conditions, suitably an aromatic hydrocarbon, e.g. benzene, toluene or xylene, especially benzene. An excess of 1,1'-carbonyldiimidazole is preferably employed.

Process (c) (iv) is suitably carried out at a temperature of from 0°C. to 50°C., preferably 10°C. to 30°C. The reaction may be carried out in an organic solvent which is inert under the reaction conditions, suitably an aromatic hydrocarbon, e.g. benzene, toluene or xylene, preferably benzene. The mole ratio of phosgene to the compound of formula IV is not particularly critical but a substantial excess of phosgene is preferably employed. The process may optionally be carried out in the presence of an acid-binding agent such as an inorganic base, e.g. sodium or potassium carbonate, or a tertiary amine, e.g. a trialkylamine or pyridine, preferably triethylamine.

Process (d) is suitably carried out in an organic solvent which is inert under the reaction conditions, at a temperature of from 0° to 120°C., typically from 15° to 100°C. and preferably from 15° to 40°C. with the proviso that the oxidation is conducted in the presence of water when Z is sulfur. The oxidation may be carried out employing any oxidizing agent suitable for converting an organic amino moiety to an imino moiety, for example an alkali metal permanganate, such as sodium or potassium permanganate, manganese dioxide and mercuric acetate, preferably potassium permanganate. Suitable solvents include aromatic solvents, such as benzene, and acyclic or cyclic ethers, such as dioxane, and lower alkanols, such as methanol and ethanol. In general, it is preferred to use an alkali metal permanganate in a solvent medium comprising water and a water-miscible organic solvent.

Process (e) is conveniently carried out at room temperature (approximately 20°C.), or at elevated temperatures up to about 100°C. Suitable organic solvents which are inert under the reaction conditions include dimethylacetamide, diethylacetamide, dimethylformamide, dimethylsulfoxide and dioxane. Preferably the compound of formula VI is a sodium or potassium salt, and the compound of formula VII is preferably the iodide.

Process (f) is conveniently effected at a temperature of from 0° to 50°C., preferably 15° to 30°C. The process may suitably be carried out in the presence of an organic solvent which is inert under the reaction conditions, such as a lower alkanol, e.g. methanol or ethanol.

Process (g) is preferably effected by alkaline hydrolysis of the compound of formula IX at a temperature of from 50° to 150°C., preferably 80° to 120°C. The preferred reagents for effecting the alkaline hydrolysis are alkali metal hydroxides such as sodium and potassium hydroxide. The reaction is conveniently carried out in an aqueous solvent medium comprising water and a water-miscible organic solvent which is inert under the reaction conditions, such as a lower alkanol, e.g. ethanol, or a cyclic ether, e.g. dioxane, and preferably dioxane.

Process (g) may also be effected by oxidative hydrolysis of the compound of formula IX, in an aqueous alkaline medium at a temperature of from 10° to 80°C., preferably 15° to 60°C. The oxidative hydrolysis is preferably effected in an alkaline medium employing a peroxide, preferably a hydroperoxide and more preferably hydrogen peroxide. The peroxide is preferably used in moderate excess, typically about 1.5 to 4 molar equivalent excess. An alkali metal hydroxide, e.g. sodium or potassium hydroxide, is suitably employed to provide the alkaline medium and is preferably employed in large excess. The alkaline oxidative hydrolysis is conveniently carried out in an aqueous solvent medium comprising water and an organic solvent which is inert under the reaction conditions, such as a lower alkanol or cyclic ether.

Process (h) is carried out in the presence of a dehydrogenating agent, such as sulfur, selenium, a benzoquinone such as 2,3,5,6-tetrachloro-1,4-benzoquinone and 2,3-dichloro-5,6-dicyano-1,4-benzoquinone, tetracyanoethylene or triphenylmethyl perchlorate or a dehydrogenation catalyst, such as palladium on charcoal or nickel. Where a dehydrogenating agent such as sulfur or a benzoquinone is used, at least 2 mols per mol of the compound X are employed, with the preferred amount being about 2 to 2.5 mols. Where a dehydrogenation catalyst is used, a catalytic amount sufficient to cause removal of two molecules of hydrogen per mole of compound of formula X is employed. Temperatures in the range of about 60° to 180°C., are employed. The particular temperatures, as well as the reaction time will depend upon the particular dehydrogenating agent or catalyst. A solvent is also used, such as xylene or other organic liquid having a sufficiently high boiling point. When a dehydrogenation catalyst is used, a hydrogen scavenger, such as nitrobenzene, is employed in place of or in addition to other solvents.

The resulting compound of the formula I may be isolated and purified from the above-described procedures using conventional techniques.

The compounds of the formulae II, IV, V, VI, VIII and IX employed as starting materials in the above-described processes (a) thru (g) may be produced from available materials by known procedures.

The compounds of the formula X employed as starting material in process (h) is preferably prepared by cyclizing the compound of the formula XI:

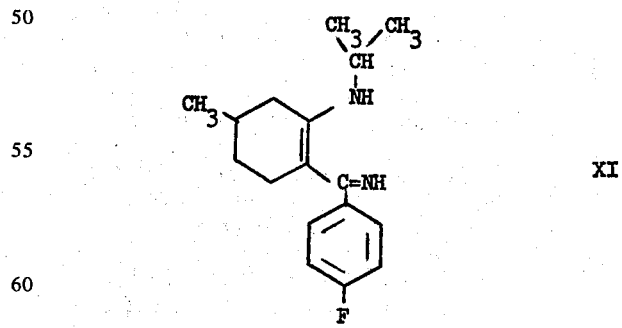

or a salt form thereof, with phosgene in a manner analogous to process (c) (iv).

The compound of the formula XI is preferably prepared by reacting the compound of the formula XII

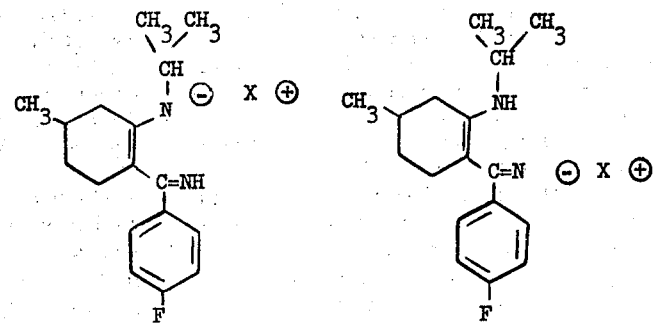

A

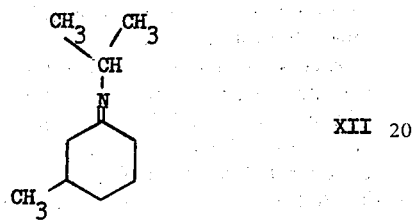

XII with the compound of the formula XIII:

XIII in the presence of a strong base, followed by quenching with water.

The preparation of compound XI by reaction of the compound XII with the compound XIII is preferably carried out in stages with the compound XII being first reacted with a strong base capable of removing a hydrogen atom from the methylene group in the cyclohexane ring adjacent to the imino function of compound XII to provide the desired anion for reaction with the compound of formula XIII. Such bases include the alkali metal salts, especially the lithium salt, of secondary amines such as diethylamine, dimethylamine and diisopropylamine, as well as other bases such as methyl magnesium iodide. Lithium diisopropylamide, because of its relatively large size, is preferred. One mol of the strong base and up to about 1.2 mols can be used per mol of the compound of formula XII, preferably equimolar amounts are used. The temperature of the reaction mixture is maintained at about 20° to 80°C. Generally, the compound of formula XII in a suitable solvent such as benzene, is added to a solution of the base in a suitable solvent and allowed to react for about 10 to 60 minutes. The compound of formula XIII, neat or in a suitable inert solvent, is then added to the reaction mixture of the base and compound XII. The resulting reaction mixture containing the salt of formula A can, at this point, be treated analogously to process (c)(iv), above, to yield directly the compound of formula X, suitable temperature control being exercised, as this reaction is exothermic. However, the salt of the formula A is advantageously quenched with water to obtain the compound of formula XI, which can be reacted in situ with phosgene to form compound X, but is preferably extracted and washed first using conventional methods.

The salt of the formula A above referred to may be represented as follows:

in which X is a metal, preferably lithium.

The compound of formula XII can be prepared by reacting a compound of formula XIV

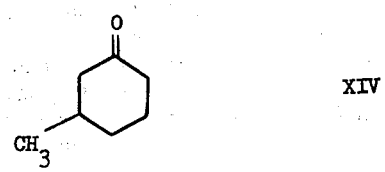

XIV with the compound of formula XV

XV to eliminate one molecule of water, conveniently in the presence of a molecular sieve or a dehydrating agent, such as alumina, calcium chloride, phosphorus pentoxide or mixtures thereof. This reaction can be carried out at temperatures from 0° to about 80°C., conveniently 20° to 30°C. Preferably, the reaction is carried out in absence of added solvents using an excess of the isopropylamine which may be later removed by vacuum distillation after removal of the dehydrating agent.

The compounds of the formulae XIII, XIV and XV are either known per se or can be produced in a known manner from available materials.

The compound of formula I is useful because it possesses pharmaceutical activity in mammals. In particular, the compound I is useful as an anti-inflammatory agent as indicated, for example, by the Carrageenan-induced edema test in rats. For the above-mentioned use, the dosage administered will, of course, vary depending upon known factors such as severity of the condition being treated and mode of administration. However, in general, satisfactory results are obtained when administered at a daily dosage of from about 0.5 milligrams to about 100 milligrams per kilogram of body weight, preferably given in divided doses 2 to 4 times a day, or in sustained release form. For most mammals, the administration of from about 40 milligrams to about 2000 milligrams of the compound per day provides satisfactory results and dosage forms suitable for internal administration comprise from about 10 milligrams to about 1000 milligrams of the compound in admixture with a solid or liquid pharmaceutical carrier or diluent.

The compound of the formula I is also useful as a potent analgesic as indicated, for example, by application of pressure to yeast-inflammed foot of the rat (oral administration). For such use, the compound may be administered to obtain satisfactory results in modes and forms similar to those employed in the treatment of inflammation and at dosages indicated above as applicable for the use of the compound in the treatment of inflammation.

The compound of the formula I may be distinguished from structurally similar quinazolinones having anti-inflammatory effect by exhibiting a high level of anti-inflammatory activity over extended periods of time following administration, as indicated by tests in higher mammals, such as man.

For the above usages, oral administration with pharmaceutically acceptable carriers may take place in such conventional forms as tablets, dispersible powders, granules, capsules, syrups and elixirs. Such compositions may be prepared according to any method known in the art for the manufacture of pharmaceutical compositions, and such compositions may contain one or more conventional adjuvants, such as sweetening agents, flavoring agents, coloring agents, and preserving agents, in order to provide an elegant and palatable preparation. Tablets may contain the active ingredient in admixture with conventional pharmaceutical excipients, e.g., inert diluents such as calcium carbonate, sodium carbonate, lactose and talc, granulating and disintegrating agents, e.g., starch and alginic acid, binding agents, e.g. magnesium stearate, stearic acid and talc. The tablets may be uncoated or coated by known techniques to delay disintegration and adsorption in the gastro-intestinal tract and thereby provide a sustained action over a longer period. Similarly, suspensions, syrups and elixirs may contain the active ingredient in admixture with any of the conventional excipients utilized for the preparation of such compositions, e.g. suspending agents (methylcellulose, tragacanth and sodium alginate), wetting agents (lecithin, polyoxyethylene stearate and polyoxyethylene sorbitan monooleate) and preservatives (ethyl-p-hydroxy-benzoate). Capsules may contain the active ingredient alone or admixed with an inert solid diluent, e.g. calcium carbonate, calcium phosphate and kaolin. The preferred pharmaceutical compositions from the standpoint of preparation and ease of administration are solid compositions, particularly hard-filled capsules and tablets.

A representative formulation is a capsule prepared by conventional techniques and containing the following ingredients:

| Ingredient | Parts by Weight |
| --- | --- |
| Compound of formula I | 50 |
| Inert solid diluent, e.g. kaolin | 200 |

EXAMPLE 1

A solution of 8.5 g. of 2-isopropylamino-4-methyl-4'-fluoro-benzophenone and 4.2 g. of potassium isocyanate in 100 ml. of glacial acetic acid is stirred at 60°–70°C. for 20 hours. The resulting mixture is treated with a mixture of ice and water and extracted three times with methylene chloride. The organic phases are combined, washed twice with water, once with sodium bicarbonate solution and again with water followed by drying and evaporation in vacuo. The residue is dissolved in a small amount of methylene chloride and precipitated by adding pentane. The resulting solid is redissolved in methylene chloride, treated with charcoal and diethyl ether exchanged for the methylene chloride to obtain a solid which is dried in a high vacuum at 60°C. to yield 1-isopropyl-7-methyl-4-(p-fluorophenyl)-2(1H)-quinazolinone, m.p. 172°–174°C.

What is claimed is:

1. The compound of the formula:

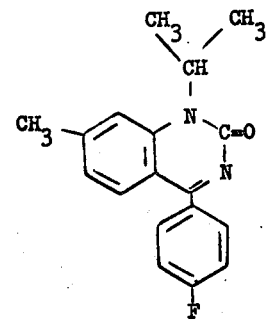

* * * * *